United States Patent
Tang et al.

(10) Patent No.: US 11,702,395 B2
(45) Date of Patent: Jul. 18, 2023

(54) BIMETAL OXIDE CATALYST AND METHODS

(71) Applicant: Xiamen University, Fujian (CN)

(72) Inventors: Xing Tang, Fujian (CN); Huai Liu, Fujian (CN); Lu Lin, Fujian (CN); Xianhai Zeng, Fujian (CN); Yong Sun, Fujian (CN)

(73) Assignee: Xiamen University, Fujian (CN)

( * ) Notice: Subject to any disclaimer, the term of this patent is extended or adjusted under 35 U.S.C. 154(b) by 112 days.

(21) Appl. No.: 17/472,243

(22) Filed: Sep. 10, 2021

(65) Prior Publication Data

US 2022/0073481 A1    Mar. 10, 2022

(30) Foreign Application Priority Data

Sep. 10, 2020   (CN) .......................... 202010947400.9

(51) Int. Cl.
| | | |
|---|---|---|
| *C07D 307/68* | (2006.01) | |
| *B01J 23/00* | (2006.01) | |
| *B01J 23/889* | (2006.01) | |
| *B01J 37/00* | (2006.01) | |
| *B01J 37/04* | (2006.01) | |
| *B01J 37/08* | (2006.01) | |

(52) U.S. Cl.
CPC .......... *C07D 307/68* (2013.01); *B01J 23/002* (2013.01); *B01J 23/8892* (2013.01); *B01J 37/0063* (2013.01); *B01J 37/04* (2013.01); *B01J 37/082* (2013.01)

(58) Field of Classification Search
CPC .................................................... C07D 307/68
USPC ....................................................... 549/485
See application file for complete search history.

(56) References Cited

FOREIGN PATENT DOCUMENTS

| CN | 104177319 A | 12/2014 |
|---|---|---|
| CN | 107987041 A | 5/2018 |
| CN | 108772062 A | 11/2018 |
| CN | 109651311 A | 4/2019 |
| CN | 109666011 A | 4/2019 |

OTHER PUBLICATIONS

Bao, et al., "Aerobic Oxidation of 5-Hydroxymethylfurfural to 2,5-Furandicarboxylic Acid over Holey 2D Mn2O3 Nanoflakes from a Mn-based MOF", ChemSusChem 2020, 13, 548-555.
Han, et al., "Selective oxidation of 5-hydroxymethylfurfural to 2,5-furandicarboxylic acid over MnOx—CeO2 composite catalysts", Green Chem., 2017, 19, 996-1004.
Rao, et al., "Inexpensive but Highly Efficient Co—Mn Mixed-Oxide Catalysts for Selective Oxidation of 5-Hydroxymethylfurfural to 2,5-Furandicarboxylic Acid", ChemSusChem 2018, 11, 3323-3334.
Zhang, et al., "Nanoscale center-hollowed hexagon MnCo2O4 spinel catalyzed aerobic oxidation of 5-hydroxymethylfurfural to 2,5-furandicarboxylic acid", Catalysis Communications 113 (2018) 19-22.
Ventura, et al., "Tunable mixed oxides based on CeO2 for the selective aerobic oxidation of 5-(hydroxymethyl)furfural to FDCA in water", Green Chem., 2018, 20, 3921-3926.
Yu et al., "M3+OIJ-Mn4+)2 clusters in doped MnOx catalysts as promoted active sites for the aerobic oxidation of 5-hydroxymethylfurfural", The Royal Society of Chemistry 2018 Technol., 2018, 8, 2299-2303.

*Primary Examiner* — Taofiq A Solola
(74) *Attorney, Agent, or Firm* — Cooper Legal Group, LLC

(57) ABSTRACT

Bimetal oxide catalyst and methods, a method comprises: mixing and grinding to obtain a mixture comprising a manganese salt (a), at least one of other metal salt (b), and an additive (c), wherein the other metal salt comprises at least one of a copper salt, a cobalt salt, a cerium salt, an iron salt, or a nickel salt, and the additive comprises at least one of polyol or organic acid, and calcining the mixture to obtain the bimetal oxide catalyst.

14 Claims, 2 Drawing Sheets

BIMETAL OXIDE CATALYST AND METHODS

RELATED APPLICATIONS

This application claims priority to Chinese patent application 202010947400.9, filed on Sep. 10, 2020. Chinese patent application 202010947400.9 is incorporated herein by reference.

FIELD OF THE DISCLOSURE

The present disclosure relates to a bimetal oxide catalyst and methods.

BACKGROUND OF THE DISCLOSURE

As a non-renewable energy source, fossil energy is gradually exhausted, and at the same time, the environmental problems caused by the large-scale use of fossil energy have become increasingly prominent. In this context, the development and utilization of renewable energy has become the only way to solve the energy crisis and environmental problems. The development and utilization of abundant and renewable biomass resources has increasingly become a research hotspot. In particular, the preparation of biomass-based polymer monomers to replace petroleum-based polymer monomers has attracted the attention of industry and academia. Among biomass-based polymer monomers, the biomass-based polyester monomer 2,5-furandicarboxylic acid has a chemical structure and physical and chemical properties similar to petroleum-based terephthalic acid, especially its polyester product polyethylene furandicarboxylate alcohol ester (PEF) with ethylene glycol shows better performance than polyethylene terephthalate (PET), so 2,5-furandicarboxylic acid and its polyester PEF are considered the most ideal bio-based alternative products to terephthalic acid and PET. At present, the catalytic oxidation of biomass-based platform molecule 5-hydroxymethylfurfural to prepare 2,5-furandicarboxylic acid is the most promising route for the synthesis of 2,5-furandicarboxylic acid, but the efficient and economical preparation of 2,5-furandicarboxylic acid is still the biggest bottleneck that hinders the large-scale industrial production of PEF, and it is urgent to develop cheap and efficient catalytic oxidation catalysts and catalytic systems.

Recently, manganese-based metal oxides, such as manganese dioxide, manganese trioxide, manganese-cobalt oxide, manganese nickel oxide, manganese cerium oxide, etc., have been widely used in the catalytic oxidation of 5-hydroxymethylfurfural to prepare 2,5-furandicarboxylic acid. Under certain reaction conditions, these catalysts can obtain a relatively good yield of 2,5-furandicarboxylic acid (85-99%) (ChemSusChem 11 (2018) 3323-3334; Catal. Sci. Technol. 8 (2018) 2299-2303; Catalysis Communications 113 (2018) 19-22; Green Chem. 19 (2017) 996-1004; Green Chem. 20 (2018) 3921-3926; ChemSusChem 13.3 (2020): 548-555). However, these catalytic systems all require pure oxygen as the oxidant. Direct use of air as an oxidant is a cheaper oxygen source option, which can effectively reduce the cost of oxidation. However, there is no report of non-precious metal catalyst that can use air as an oxidant to catalyze the oxidation of 5-hydroxymethylfurfural to produce 2,5-furandicarboxylic acid. At the same time, the preparation process of the above-mentioned manganese-based oxide catalyst is relatively complicated, and it is not easy to realize large-scale preparation. The catalytic efficiency of these manganese-based oxides is relatively low, and it is necessary to develop a new catalyst preparation method to improve the activity of the catalyst. In addition, traditional catalyst preparation generally adopts hydrothermal treatment, and a large amount of wastewater is often produced in the process. The treatment of this wastewater will increase the production cost of 2,5-furandicarboxylic acid.

BRIEF SUMMARY OF THE DISCLOSURE

An objective of the present disclosure is to provide a method for preparing a bimetal oxide catalyst, which comprises the following steps.

Mixing and grinding a manganese salt (a), other metal salt (b), and an additive (c) (e.g., in an agate mortar) to obtain a mixture (e.g., a uniform mixture), wherein the other metal salt comprises at least one of a copper salt, a cobalt salt, a cerium salt, an iron salt, or a nickel salt, and the additive comprises at least one of polyol or organic acid, and calcining the mixture to obtain the bimetal oxide catalyst.

In a preferred embodiment, the manganese salt comprises, but is not limited to, at least one of manganese nitrate, manganese acetate, or manganese oxalate.

In a preferred embodiment, the copper salt comprises at least one of copper nitrate, copper acetate, or copper oxalate, the cobalt salt comprises at least one of cobalt nitrate, cobalt acetate, or cobalt oxalate, the cerium salt comprises at least one of cerium nitrate, cerium acetate, or cerium oxalate, the iron salt comprises at least one of iron nitrate, iron acetate, or iron oxalate, and the nickel salt comprises at least one of nickel nitrate, nickel acetate, or nickel oxalate.

In a preferred embodiment, calcining the mixture comprises calcining the mixture at 160-240° C. for 0.5-5 hours to obtain the bimetal oxide catalyst, wherein a molar ratio of a to b is 1:(0.1-2), and a molar ratio of c to a sum of (a+b) is 0.1-(0.4:1)

In a preferred embodiment, calcining the mixture comprises calcining the mixture at 160-240° C. for 0.5-5 hours comprises calcining the mixture at 180-220° C. for 1-3 hours.

In a preferred embodiment, the polyol comprises at least one of vitamin C, citric acid, or malic acid, and the organic acid comprises at least one of fructose, glucose, or xylose.

In a preferred embodiment, calcining the mixture comprises calcining the mixture in an air atmosphere.

Another objective of the present disclosure is to provide the bimetal oxide catalyst prepared by the method.

Another objective of the present disclosure is to provide a method for catalytically oxidizing 5-hydroxymethylfurfural to prepare 2,5-furandicarboxylic acid using the bimetal oxide catalyst.

Furthermore another objective of the present disclosure is to provide a method for catalytically oxidizing 5-hydroxymethylfurfural (HMF) to prepare 2,5-furandicarboxylic acid, comprising: mixing the 5-hydroxymethylfurfural, alkali, and solvent to obtain a mixture, charging the mixture in a reaction container, and adding the bimetal oxide catalyst to obtain a reaction solution; a HMF oxidation is performed after sealing the reaction container, using air or oxygen to function as an oxygen source; after the HMF oxidation is completed, a pH of the reaction solution is tuned to be acidic using concentrated hydrochloric acid to obtain the 2,5-furandicarboxylic acid. The reaction conditions for the HMF oxidation are as follows: a reaction temperature is 100-150° C., a time is 0.5-5 hours, a pressure of the reaction container is 5-30 bar, a concentration of the 5-hydroxymethylfurfural in the solvent is 0.5-20 wt %, a mass ratio of the bimetal oxide catalyst to the 5-hydroxymethylfurfural is (0.2-3):1, and a molar ratio of the alkali to the 5-hydroxymethylfurfural is (0.1-3):1.

In a preferred embodiment, the reaction temperature is 110-130° C., the time is 1-3 hours, the pressure of the reaction container is 10-30 bar, the concentration of the 5-hydroxymethylfurfural in the solvent is 0.5-20 wt %, the mass ratio of the bimetal oxide catalyst to the 5-hydroxymethylfurfural is (0.5-2):1, and a molar ratio of the alkali to the 5-hydroxymethylfurfural is (0.5-2):1.

In a preferred embodiment, the alkali is at least one of sodium hydroxide, sodium carbonate, potassium carbonate, sodium bicarbonate, potassium bicarbonate, or calcium hydroxide.

In a preferred embodiment, the solvent is at least one of water or a mixed solvent system, and the mixed solvent system consists of water and organic solvent, wherein a ratio of the organic solvent to the water is (1:10)-(10:1).

In a preferred embodiment, the organic solvent comprises, but is not limited to, at least one of dimethyl sulfoxide, acetonitrile, or 1,4-dioxane.

Compared with the background technology, this technical solution has the following advantages:

1. The bimetal oxide catalyst prepared by the present disclosure enables air to function as an oxidant to effectively oxidize 5-hydroxymethylfurfural to obtain 2,5-furandicarboxylic acid.

2. The present disclosure provides a method for preparing a manganese-based metal oxide (i.e., the bimetal oxide catalyst) that is rich in surface oxygen vacancies. The method is solvent-free, simple, and environmentally friendly, which easily enables the preparation of the catalyst at a larger scale. In this method, the manganese-based metal oxide catalyst can be obtained after a simple grinding process and calcination. The introduction of proper additives can effectively increase a content of the oxygen vacancies on the surface of the catalyst, thereby greatly improving a catalytic oxidation activity of the catalyst.

3. The present disclosure provides the method for preparing a manganese-based non-noble metal oxide to function as a catalyst, and the method is solvent-free and simple, which easily enables the preparation of the catalyst at a larger scale. The preparation process does not use solvents, acids, alkalis, and other expensive and polluting chemical reagents, and the preparation process is an economical and environmentally friendly preparation process. The prepared manganese-based metal oxide catalyst can use cheap and easily available air to function as an oxygen source (when pure oxygen is used, a catalytic efficiency is higher), and it can efficiently and catalytically oxidize 5-hydroxymethylfurfural to synthesize 2,5-furandicarboxylic acid under mild reaction conditions.

BRIEF DESCRIPTION OF THE DRAWINGS

The present disclosure will be further described in combination with the accompanying embodiments and drawings.

DETAILED DESCRIPTION OF THE EMBODIMENTS

Figure 1:
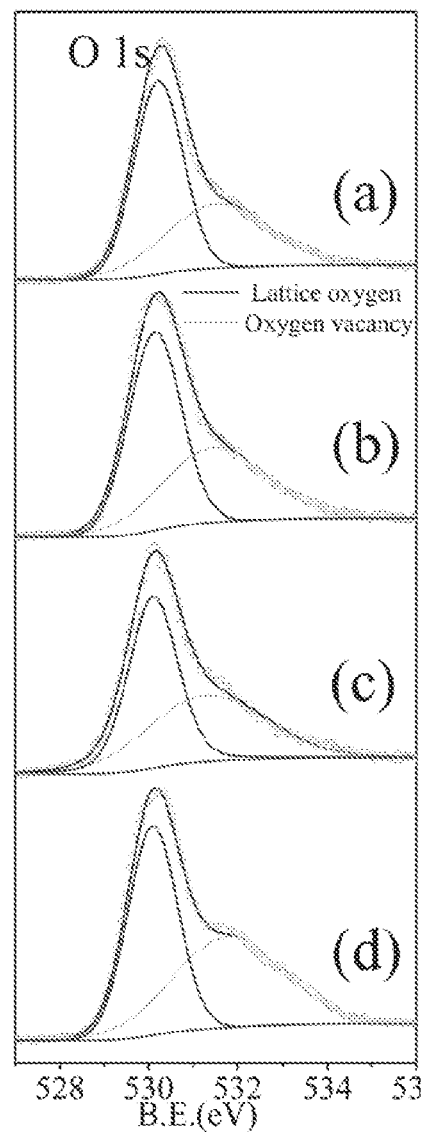
FIG. 1 illustrates an O1s X-ray photoelectron spectroscopy (XPS) high-resolution spectrum of a manganese-cobalt bimetal oxide catalyst.

The present disclosure will be further described in combination with the accompanying embodiments and drawings.

Embodiment 1

Preparation of a manganese-cobalt bimetal oxide catalyst: manganese nitrate a (6 mmol), cobalt nitrate b (4 mmol), and an additive c (vitamin C, 1 mmol) are uniformly mixed and grinded, wherein a molar ratio of a to b is 3/2, and a molar ratio of c to a sum of (a+b) is 0.1. The mixture is calcined at 200° C. for 2 hours in an air atmosphere to obtain the manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave (e.g., a reaction container), and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 revolutions per minute (rpm)) and is maintained for 3 hours to complete the reaction. High-performance liquid chromatography (HPLC) (Water 2695) is used to carry out qualitative analysis and quantitative analysis. Analysis results are listed in Table 1 and assigned a serial number of 1.

Embodiment 2

Preparation of a manganese-cobalt bimetal oxide catalyst: manganese nitrate a (6 mmol), cobalt nitrate b (4 mmol), and an additive c (vitamin C, 2 mmol) are uniformly mixed and grinded, wherein a molar ratio of a to b is 3/2, and a molar ratio of c to a sum of (a+b) is 0.2. The mixture is calcined at 200° C. for 2 hours in an air atmosphere to obtain the manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 2.

Embodiment 3

Preparation of a manganese-cobalt bimetal oxide catalyst: manganese nitrate a (6 mmol), cobalt nitrate b (4 mmol), and an additive c (vitamin C, 3 mmol) are uniformly mixed and grinded, wherein a molar ratio of a to b is 3/2, and a molar ratio of c to a sum of (a+b) is 0.3. The mixture is calcined at 200° C. for 2 hours in an air atmosphere to obtain the manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 3.

Embodiment 4

Preparation of a manganese-cobalt bimetal oxide catalyst: manganese nitrate a (8 mmol), cobalt nitrate b (2 mmol), and an additive c (vitamin C, 3 mmol) are uniformly mixed and grinded, wherein a molar ratio of a to b is 4/1, and a molar ratio of c to a sum of (a+b) is 0.3. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 4.

Embodiment 5

Preparation of a manganese-cobalt bimetal oxide catalyst: manganese nitrate a (4 mmol), cobalt nitrate b (6 mmol), and an additive c (vitamin C, 3 mmol) are uniformly mixed and grinded, wherein a molar ratio of a to b is 2/3, and a molar ratio of c to a sum of (a+b) is 0.3. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 5.

Embodiment 6

Preparation of a manganese-cobalt bimetal oxide catalyst: manganese nitrate a (6 mmol), cobalt nitrate b (4 mmol), and an additive c (citric acid, 3 mmol) are uniformly mixed and grinded, wherein a molar ratio of a to b is 3/2, and a molar ratio of c to a sum of (a+b) is 0.3. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 6.

Embodiment 7

Preparation of a manganese-cobalt bimetal oxide catalyst: manganese nitrate a (6 mmol), cobalt nitrate b (4 mmol), and an additive c (malic acid, 3 mmol) are uniformly mixed and grinded, wherein a molar ratio of a to b is 3/2, and a molar ratio of c to a sum of (a+b) is 0.3. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 7.

Embodiment 8

Preparation of a manganese-cobalt bimetal oxide catalyst: manganese nitrate a (6 mmol), cobalt nitrate b (4 mmol), and an additive c (fructose, 2 mmol) are uniformly mixed and grinded, wherein a molar ratio of a to b is 3/2, and a molar ratio of c to a sum of (a+b) is 0.2. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 8.

Embodiment 9

Preparation of a manganese-cobalt bimetal oxide catalyst: manganese nitrate a (6 mmol), cobalt nitrate b (4 mmol), and an additive c (glucose, 1 mmol) are uniformly mixed and grinded, wherein a molar ratio of a to b is 3/2, and a molar ratio of c to a sum of (a+b) is 0.1. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 9.

Embodiment 10

Preparation of a manganese-cobalt bimetal oxide catalyst: manganese nitrate a (6 mmol), cobalt nitrate b (4 mmol), and an additive c (glucose, 2 mmol) are uniformly mixed and grinded, wherein a molar ratio of a to b is 3/2, and a molar ratio of c to a sum of (a+b) is 0.2. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 10.

Embodiment 11

Preparation of a manganese-cobalt bimetal oxide catalyst: manganese nitrate a (6 mmol), cobalt nitrate b (4 mmol), and an additive c (xylose, 2 mmol) are uniformly mixed and grinded, wherein a molar ratio of a to b is 3/2, and a molar ratio of c to a sum of (a+b) is 0.2. The mixture is calcined at 200° C. for 2 hours in an air atmosphere to obtain a manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 11.

Embodiment 12

Preparation of a manganese-copper bimetal oxide catalyst: manganese nitrate a (6 mmol), copper nitrate b (4 mmol), and an additive c (vitamin C, 3 mmol) are uniformly mixed and grinded, wherein a molar ratio of a to b is 3/2, and a molar ratio of c to a sum of (a+b) is 0.3. The mixture is calcined at 200° C. for 2 hours in an air atmosphere to obtain a manganese-copper bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-copper bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 12.

Embodiment 13

Preparation of a manganese-cerium bimetal oxide catalyst: manganese nitrate a (12 mmol), cerium nitrate b (2 mmol), and an additive c (vitamin C, 4.2 mmol) are uniformly mixed and grinded, wherein a molar ratio of a to b is 6/1, and a molar ratio of c to a sum of (a+b) is 0.3. The mixture is calcined at 200° C. for 2 hours in an air atmosphere to obtain a manganese-cerium bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cerium bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 13.

Embodiment 14

Preparation of a manganese-iron bimetal oxide catalyst: manganese nitrate a (12 mmol), iron nitrate b (2 mmol), and an additive c (vitamin C, 4.2 mmol) are uniformly mixed and grinded, wherein a molar ratio of a to b is 6/1, and a molar ratio of c to a sum of (a+b) is 0.3. The mixture is calcined at 200° C. for 2 hours in an air atmosphere to obtain a manganese-iron bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-iron bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 14.

Embodiment 15

Preparation of a manganese-nickel bimetal oxide catalyst: manganese nitrate a (10 mmol), nickel nitrate b (1 mmol), and an additive c (vitamin C, 3.3 mmol) are uniformly mixed and grinded, wherein a molar ratio of a to b is 10/1, and a molar ratio of c to a sum of (a+b) is 0.3. The mixture is calcined at 200° C. for 2 hours in an air atmosphere to obtain a manganese-nickel bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-nickel bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 15.

Embodiments 16-18

0.3 g of 5-hydroxymethylfurfural, 0.4 g of sodium bicarbonate (two molar equivalents of 5-hydroxymethylfurfural), and 2.7 g of a mixed solvent of water/dimethyl sulfoxide (wherein a mass ratio of water to dimethyl sulfoxide is 1:2), water/acetonitrile (wherein a mass ratio of water to acetonitrile is 1:10), and water/1,4-dioxane (wherein a mass ratio of water to 1,4-dioxane is 1:10) are added into a 20 mL autoclave, and the manganese-cobalt bimetal oxide catalyst (0.6 g) prepared in Embodiment 3 is then added to function as a catalyst. The autoclave is sealed, oxygen is introduced, a pressure of the autoclave is increased to 30 bar, and the mixture is vigorously stirred (500 rpm). The autoclave is heated to 130° C. and is maintained for 3 hours. After the reaction is completed, the reaction products are cooled to room temperature (i.e., 20-30° C.), and a sample is taken. HPLC (Water 2695) is used for qualitative analysis and quantitative analysis. Analysis results are listed in Table 1 and assigned serial numbers of 16-18.

Embodiments 19-23

0.03 g of 5-hydroxymethylfurfural, 3 g of water, 0.02 g of sodium hydroxide, 0.02 g of calcium hydroxide, 0.025 g of sodium carbonate, 0.03 g of potassium carbonate, or 0.05 g of potassium bicarbonate are added into a 20 mL autoclave, and the manganese-cobalt bimetal oxide catalyst (0.06 g) prepared in Embodiment 3 is then added to function as a catalyst. The autoclave is sealed, air is introduced, a pressure of the autoclave is increased to 15 bar, and the mixture is vigorously stirred (500 rpm). The autoclave is heated to 130° C. and is maintained for 3 hours. After the reaction is completed, the reaction products are cooled to room temperature, and a sample is taken. HPLC (Water 2695) is used for qualitative analysis and quantitative analysis. Analysis results are listed in Table 1 and assigned serial numbers of 19-23.

Embodiments 24-26

0.03 g of 5-hydroxymethylfurfural, 3 g of water, and 0.04 g of sodium bicarbonate are added into a 20 mL autoclave, and the manganese-cobalt bimetal oxide catalyst (0.6 g) prepared in Embodiment 3 is then added to function as a catalyst. The autoclave is sealed, air is introduced, a pressure of the autoclave is increased to 15 bar, and the mixture is vigorously stirred (500 rpm). The autoclave is heated to 110° C., 120° C., or 140° C. and is maintained for 3 hours. After the reaction is completed, the reaction products are cooled to room temperature, and a sample is taken. HPLC (Water 2695) is used for qualitative analysis and quantitative analysis. Analysis results are listed in Table 1 and assigned serial numbers of 24-26.

Embodiments 27-29

0.03 g of 5-hydroxymethylfurfural, 3 g of water, and 0.04 g of sodium bicarbonate are added into a 20 mL autoclave, and the manganese-cobalt bimetal oxide catalyst (0.6 g) prepared in Embodiment 3 is then added to function as a catalyst. The autoclave is sealed, air is introduced, a pressure of the autoclave is increased to 5 bar, 10 bar, or 30 bar, and the mixture is vigorously stirred (500 rpm). The autoclave is heated to 130° C. and is maintained for 3 hours. After the reaction is completed, the reaction products are cooled to room temperature, and a sample is taken. HPLC (Water 2695) is used for qualitative analysis and quantitative analysis. Analysis results are listed in Table 1 and assigned serial numbers of 27-29.

Embodiment 30-31

Preparation of a manganese-cobalt bimetal oxide catalyst: manganese acetate or manganese oxalate a (6 mmol), cobalt nitrate b (4 mmol), and an additive c (vitamin C, 3 mmol) are uniformly mixed and grinded, wherein a molar ratio of a to b is 3/2, and a molar ratio of c to a sum of (a+b) is 0.3. The mixture is calcined at 200° C. for 2 hours in an air atmosphere to obtain the manganese-cobalt bimetal oxide catalyst.

Process of 5-hydroxymethylfurfural oxidation reaction: 0.03 g of 5-hydroxymethylfurfural, 0.04 g of sodium bicarbonate, and 3 g of water are added into a 20 mL autoclave, and 0.06 g of the manganese-cobalt bimetal oxide catalyst is then added to function as a catalyst. After the autoclave is sealed, air is introduced, a pressure of the autoclave is increased to 15 bar, and the autoclave is then heated to 130° C. simultaneously with vigorous stirring (500 rpm) and is maintained for 3 hours to complete the reaction. HPLC (Water 2695) is used to carry out qualitative analysis and quantitative analysis. Analysis results are listed in Table 1 and assigned a serial number of 30-31.

TABLE 1

The analysis results of the embodiments

HMF →[O]→ DFF or

HMFCA →|O|→ FFCA →|O|→ FDCA

| Embodiments | a/b | c/a sum of (a + b) | Reaction conditions | HMF conversion rate (%) | rate (%) FFCA | FDCA |
|---|---|---|---|---|---|---|
| 1 | 3/2 | 0.1 | | 100 | 33 | 36 |
| 2 | 3/2 | 0.2 | | 100 | 0 | 91 |
| 3 | 3/2 | 0.3 | | 100 | 0 | 96 |
| 4 | 4/1 | 0.3 | | 100 | 17 | 70 |
| 5 | 2/3 | 0.3 | | 100 | 21 | 42 |
| 6 | 3/2 | 0.3 | | 100 | 0 | 72 |
| 7 | 3/2 | 0.3 | | 100 | 0 | 86 |
| 8 | 3/2 | 0.2 | air, 15 bar, 130° C., 3 hours | 100 | 0 | 71 |
| 9 | 3/2 | 0.1 | | 100 | 19 | 46 |
| 10 | 3/2 | 0.2 | | 100 | 0 | 73 |
| 11 | 3/2 | 0.2 | | 100 | 0 | 81 |
| 12 | 3/2 | 0.3 | | 100 | 12 | 81 |
| 13 | 6/1 | 0.3 | | 100 | 5 | 88 |
| 14 | 6/1 | 0.3 | | 100 | 0 | 91 |
| 15 | 10/1 | 0.3 | | 100 | 12 | 80 |
| 16 | | | air, 30 bar, 130° C., 3 hours | 100 | 25 | 53 |
| 17 | | | air, 30 bar, 130° C., 3 hours | 100 | 10 | 76 |
| 18 | | | air, 30 bar, 130° C., 3 hours | 100 | 0 | 85 |
| 19 | | | | 100 | 0 | 45 |
| 20 | | | | 100 | 0 | 53 |
| 21 | | | air, 15 bar, 130° C., 3 hours | 100 | 0 | 89 |
| 22 | 3/2 | 0.3 | | 100 | 0 | 85 |
| 23 | | | | 100 | 0 | 93 |
| 24 | | | air, 15 bar, 110° C., 3 hours | 100 | 23 | 62 |
| 25 | | | air, 15 bar, 120° C., 3 hours | 100 | 8 | 83 |
| 26 | | | air, 15 bar, 140° C., 3 hours | 100 | 0 | 96 |
| 27 | | | air, 5 bar, 140° C., 3 hours | 100 | 23 | 38 |
| 28 | | | air, 10 bar, 130° C., 3 hours | 100 | 5 | 82 |
| 29 | | | air, 30 bar, 130° C., 3 hours | 100 | 0 | 94 |
| 30 | 3/2 | 0.3 | air, 15 bar, 130° C., 3 hours | 100 | 0 | 93 |
| 31 | | | | 100 | 0 | 95 |

TABLE 2

Relative content of surface oxygen vacancies of the manganese-cobalt bimetal oxide catalyst obtained from an integration of the O1s XPS high-resolution spectrum in FIG. 1. (Referring to FIG. 1 and Table 2, an addition of vitamin C can significantly increase the relative content of oxygen vacancies of the catalytic surface)

| No | catalyst | Materials for preparing the manganese-cobalt bimetal oxide catalyst | Relative content of the oxygen vacancies (%) |
|---|---|---|---|
| 1 | a | manganese nitrate (6 mmol), cobalt nitrate (4 mmol) | 41.4 |
| 2 | b | manganese nitrate (6 mmol), cobalt nitrate (4 mmol), VC (1 mmol) | 43.5 |
| 3 | c | manganese nitrate (6 mmol), cobalt nitrate (4 mmol), VC (2 mmol) | 45.6 |
| 4 | d | manganese nitrate (6 mmol), cobalt nitrate (4 mmol), VC (3 mmol) | 49.7 |

Figure 2A:
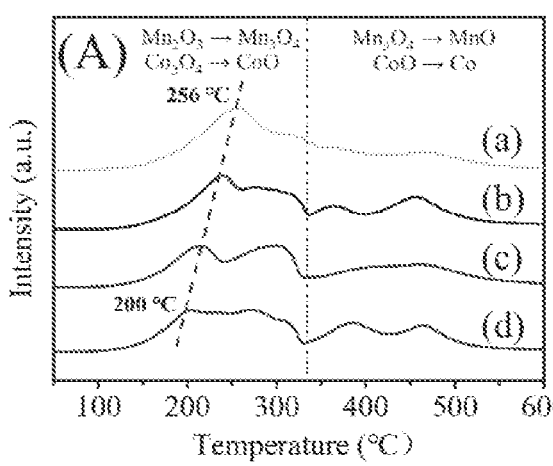
FIG. 2A illustrates a $H_2$-temperature programmed reduction ($H_2$-TPR) spectrum of the manganese-cobalt bimetal oxide catalyst.
Figure 2B:
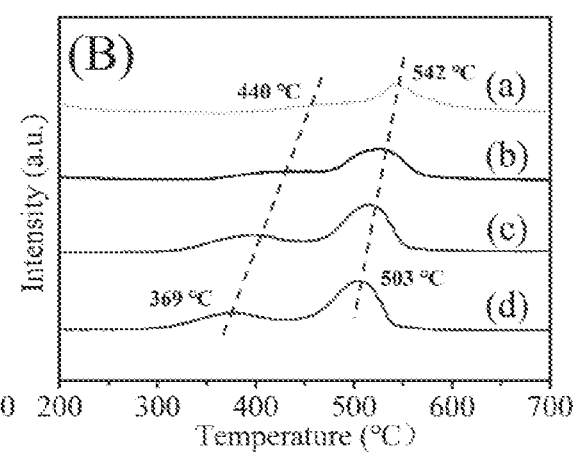
FIG. 2B illustrates an $O_2$-temperature programmed desorption ($O_2$-TPD) spectrum of the manganese-cobalt bimetal oxide catalyst.

Referring to FIG. 2, the H$_2$-TPR spectrum (FIG. 2A) shows that the addition of vitamin C makes the catalyst easily reduce, namely the manganese-cobalt bimetal oxide catalyst easily loses lattice oxygen, and an activity of the lattice oxygen becomes higher. The $O_2$-TPD spectrum (FIG. 2B) verifies the aforementioned point again.

The aforementioned embodiments are merely some embodiments of the present disclosure, and the scope of the disclosure is not limited thereto. Thus, it is intended that the present disclosure cover any modifications and variations of the presently presented embodiments provided they are made without departing from the appended claims and the specification of the present disclosure.

What is claimed is:

1. A method for preparing a bimetal oxide catalyst, comprising:
    mixing and grinding a manganese salt (a), other metal salt (b), and an additive (c) to obtain a mixture, wherein the other metal salt (b) comprises at least one of a copper salt, a cobalt salt, a cerium salt, an iron salt, or a nickel salt, and the additive (c) comprises at least one of polyol or organic acid, and
    calcining the mixture to obtain the bimetal oxide catalyst.

2. The method according to claim 1, wherein the manganese salt (a) comprises at least one of manganese nitrate, manganese acetate, or manganese oxalate.

3. The method according to claim 1, wherein:
    the copper salt comprises at least one of copper nitrate, copper acetate, or copper oxalate,
    the cobalt salt comprises at least one of cobalt nitrate, cobalt acetate, or cobalt oxalate,
    the cerium salt comprises at least one of cerium nitrate, cerium acetate, or cerium oxalate,
    the iron salt comprises at least one of iron nitrate, iron acetate, or iron oxalate, and
    the nickel salt comprises at least one of nickel nitrate, nickel acetate, or nickel oxalate.

4. The method according to claim 1, wherein:
    the polyol comprises at least one of vitamin C, citric acid, or malic acid, and
    the organic acid comprises at least one of fructose, glucose, or xylose.

5. The method according to claim 1, wherein:
    calcining the mixture comprises calcining the mixture at 160-240° C. for 0.5-5 hours to obtain the bimetal oxide catalyst, and
    a molar ratio of a to b is 1:(0.1-2), and a molar ratio of c to a sum of (a+b) is (0.1-0.4):1.

6. The method according to claim 1, wherein calcining the mixture comprises calcining the mixture at 180-220° C. for 1-3 hours.

7. The method according to claim 1, wherein calcining the mixture comprises calcining the mixture in an air atmosphere.

8. The bimetal oxide catalyst prepared by the method according to claim 1.

9. A method for catalytically oxidizing 5-hydroxymethylfurfural to prepare 2,5-furandicarboxylic acid using the bimetal oxide catalyst according to claim 8.

10. A method for catalytically oxidizing 5-hydroxymethylfurfural to prepare 2,5-furandicarboxylic acid, comprising:
    mixing the 5-hydroxymethylfurfural, alkali, and solvent to obtain a mixture, charging the mixture in a reaction container,
    adding the bimetal oxide catalyst according to claim 8 to obtain a reaction solution, using air or oxygen to function as an oxygen source, and
    reacting to obtain the 2,5-furandicarboxylic acid,
    wherein a reaction temperature is 100-150° C., a time is 0.5-5 hours, a pressure of the reaction container is 5-30 bar, a concentration of the 5-hydroxymethylfurfural in the solvent is 0.5-20 wt %, a mass ratio of the bimetal oxide catalyst to the 5-hydroxymethylfurfural is (0.2-3):1, and a molar ratio of the alkali to the 5-hydroxymethylfurfural is (0.1-3):1.

11. The method according to claim 10, wherein the alkali comprises at least one of sodium hydroxide, sodium carbonate, potassium carbonate, sodium bicarbonate, potassium bicarbonate, or calcium hydroxide.

12. The method according to claim 10, wherein:
    the solvent is at least one of water or a mixed solvent system, and
    the mixed solvent system consists of water and organic solvent, wherein a ratio of the organic solvent to the water is (1:10)-(10:1).

13. The method according to claim 12, wherein the organic solvent comprises at least one of dimethyl sulfoxide, acetonitrile, or 1,4-dioxane.

14. The method according to claim 12, comprising tuning a pH of the reaction solution to be acidic using hydrochloric acid to obtain the 2,5-furandicarboxylic acid after the reacting.

* * * * *